United States Patent [19]

Merkel et al.

[11] 4,393,072
[45] Jul. 12, 1983

[54] THIENYLBENZOIC ACID DERIVATIVES

[75] Inventors: Wulf Merkel; Dieter Bormann; Dieter Mania, all of Kelkheim; Roman Muschaweck, Frankfurt am Main, all of Fed. Rep. of Germany

[73] Assignee: Hoechst Aktiengesellschaft, Frankfurt am Main, Fed. Rep. of Germany

[21] Appl. No.: 418,649

[22] Filed: Sep. 16, 1982

Related U.S. Application Data

[63] Continuation of Ser. No. is a continuation of Ser. No. 94,059, Nov. 14, 1979, abandoned.

[30] Foreign Application Priority Data

Nov. 16, 1978 [DE] Fed. Rep. of Germany ....... 2849646

[51] Int. Cl.³ .................. A61K 31/38; C07D 333/24
[52] U.S. Cl. .................................. 424/275; 549/59; 549/60; 549/77
[58] Field of Search .................... 549/59, 60, 77; 424/275

[56] References Cited

U.S. PATENT DOCUMENTS 3,758,522 9/1973 Feit et al. ............... 549/77
3,780,027 12/1973 Crogoe et al. ........... 549/77
3,806,534 4/1974 Feit ...................... 549/77
3,819,692 6/1974 Feit et al. ............... 549/77
3,950,380 4/1976 Feit et al. ............... 549/77

FOREIGN PATENT DOCUMENTS 2654795 7/1977 Fed. Rep. of Germany .

*Primary Examiner*—Alan Siegel
*Attorney, Agent, or Firm*—Curtis, Morris & Safford

[57] ABSTRACT

The invention provides thienylbenzoic acid derivatives of the formula I

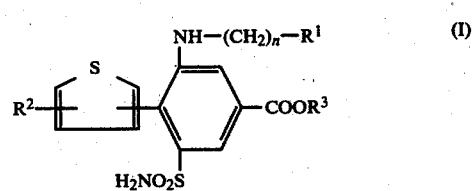

in which $R^1$ is an alkyl radical having from 1 to 3 carbon atoms, a phenyl, thienyl or furyl radical optionally substituted by halogen, $CF_3$, $CH_3$ or $OCH_3$; $R^2$ is hydrogen, halogen or $CH_3$; $R^3$ is hydrogen or alkyl having from 1 to 4 carbon atoms or benzyl; and n is 1 or 2; and the pharmaceutically tolerable salts thereof with acids or bases.

9 Claims, No Drawings

THIENYLBENZOIC ACID DERIVATIVES

This is a continuation of application Ser. No. 247,401 filed Mar. 25, 1981, now abandoned, which in turn is a continuation of application Ser. No. 94,059 filed Nov. 14, 1979, now abandoned.

Subject of the invention are thienylbenzoic acid derivatives of the formula I

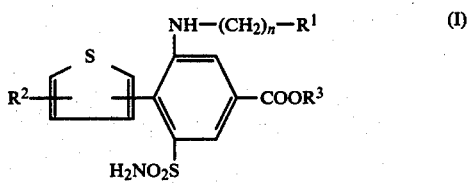

in which $R^1$ is an alkyl radical having from 1 to 3 carbon atoms, a phenyl, thienyl or furyl radical optionally substituted by halogen, $CF_3$, $CH_3$ or $OCH_3$; $R^2$ is hydrogen, halogen or $CH_3$; $R^3$ is hydrogen or alkyl having from 1 to 4 carbon atoms or benzyl; and n is 1 or 2; and the pharmaceutically tolerable salts thereof with acids or bases.

Subject of the invention is furthermore a process for the preparation of the compound of formula I, which comprises reacting compounds of the formula II

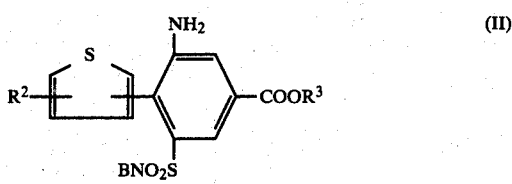

in which $R^2$ and $R^3$ are as defined above, and B represents 2 hydrogen atoms or the $(CH_3)_2N-CH=$ group, with compounds of the formula III $$R^1-(CH_2)_n-Y \qquad (III)$$

in which $R^1$ and n are as defined above and Y is a leaving-group; or condensing them with aldehydes of the formula IV

in which m is zero or 1, and reducing the azomethines obtained either simultaneously or subsequently; or reducing compounds of the formula V

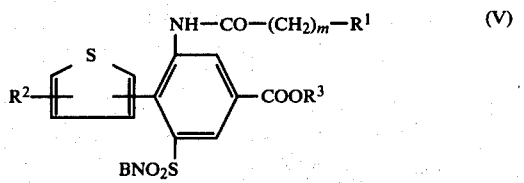

in which $R^1$ to $R^3$, B and m are as defined above, with diborane or complex boron hydrides, optionally in the presence of Lewis acids, and optionally hydrolizing thereafter the compounds so obtained, and optionally converting them to their salts by treatment with corresponding pharmaceutically tolerable acids or bases.

Especially important are compounds of the formula I, in which $R^1$ is phenyl, 2-, 3- or 4-fluorophenyl, 2- or 3-thienyl, 2- or 3-furyl, and $R^2$ is hydrogen or methyl.

The process of the invention relates to monosubstitution of the compounds of formula II according to usual methods. In the alkylation of the compounds II with alkylation agents of the formula III, there are used as leaving-group Y especially halogen, preferably bromine, a hydroxy or sulfonyloxy, alkyl or arylsulfonyloxy group. The reaction is optionally carried out in the presence of a base in order to bind the acid set free; organic tertiary amines such as trimethylamine, triethylamine or pyridine being preferably used in this case. Suitable inorganic bases are preferably sodium bicarbonate or potassium carbonate.

In the monosubstitution via the azomethines, aldehydes of the formula IV are employed, and the usual processes for preparing azomethine (Schiff's base) are applied. The azomethines obtained are reduced either simultaneously by catalytic hydrogenation of the aldehydes of formula IV in the presence of the amines of formula II, or after complete condensation by reduction in known manner, for example with sodium borohydride, while using the solvents normally employed for such a reduction, for example lower aliphatic alcohols etc.

Preparation of the compounds of formula I by reduction of the amido compounds of formula V may be carried out according to the operation mode described in German Offenlegungsschriften Nos. 2 345 229 and 2 453 548. The reduction is carried out either with diborane or with complex boron hydrides in the presence of Lewis acids, or with diborane alone; especially advantageous is a combination of sodium borohydride and boron trifluoride. The reaction conditions are described in detail in the above German Offenlegungsschriften.

In all process variants, it is especially recommended to protect the sulfamyl group by the protective group B, thus preventing side reactions at the sulfonamide group. After the amino group has been substituted, the protective group B can be split off by basic or acidic hydrolysis; optionally, a possibly present ester group $COOR^3$ being converted simultaneously to the free carboxyl group.

The starting substances of formula II are known from German Offenlegungsschrift No. 2 654 795, or they can be prepared in analogous manner. When starting compounds of formula II in which B represents 2 hydrogen atoms are used, the protective group can be split off from the above compounds by alkaline or acidic hydrolysis.

The starting substances of formula V are prepared according to the acylation processes described in German Offenlegungsschriften Nos. 2 345 229 and 2 453 548. The amines of formula II are converted under the reaction conditions described in the cited German Offenlegungsschriften to the amido compounds of formula V by means of carboxylic acid derivatives suitable for the formation of amides, especially chlorides or esters.

The final product of formula I obtained according to the above processes are capable of forming salts with pharmaceutically tolerable acids or bases such as they are usually employed in this field.

The sulfamoylbenzoic acid derivatives of formula I and their pharmaceutically tolerable salts are highly active diuretics and salidiuretics which may be applied as pharmaceuticals in human and veterinary medicine, in doses of from 0.5 to 100 mg, in the form of capsules, dragees, tablets or solutions containing different additives, either enterally (for example orally by means of a probe) or parenterally (injection into the vascular system, for example intravenous injection or injection into the muscles or under the skin etc.). They are suitable for treating oedemas such as cardiac, renal or hepatic oedemas, and other such symptoms based on disturbances of the water and electrolyte balance. The compounds may be applied per se, in combination with other salidiuretically active substances, even those having another activity range, or with different other medicaments either separately, alternately or in combination. Especially, SPIRONOLACTONE, TRIAMTERENE, AMILORIDE and other K+-retaining compounds can be used alternately with long-acting salidiuretics of the CHLOROTHALIDONE type or other potassium-containing compounds which compensate K+ losses (salts and the like).

Apart from the compounds described in the Examples, the following compounds of the invention are especially interesting:

3-(4-fluorobenzylamino)-4-(2-thieny)-5-sulfamoyl-benzoic acid 3-(4-fluorobenzylamino)-4-(3-thienyl)-5sulfamoyl-benzoic acid 3-(3-fluorobenzylamino)-4-(2-thienyl)-5-sulfamoyl-benzoic acid 3-(3-fluorobenzylamino)-4-(3-thienyl)-5-sulfamoyl-benzoic acid 3-(2-fluorobenzylamino)-4-(2-thienyl)-5-sulfamoyl-benzoic acid 3-(2-fluorobenzylamino-4-(3-thienyl)-5-sulfamoyl-benzoic acid 3-(4-methylbenzylamino)-4-(2-thienyl)-5-sulfamoyl-benzoic acid 3-(4-methylbenzylamino)-4-(3-thienyl)-5-sulfamoyl-benzoic acid 3-(3'-thenylamino)-4-(5-methyl-2-thienyl)-5-sulfamoylbenzoic acid 3-(3-thenylamino)-4-(5-methyl-3-thienyl)-5-sulfamoylbenzoic acid 3-(2'-thenylamino)-4-(5-methyl-2-thienyl)-5-sulfamoylbenzoic acid 3-(2'-thenylamino)-4-(5-methyl-3-thienyl)-5-sulfamoylbenzoic acid 3-(2-methoxybenzylamino)-4-(2-thienyl)-5-sulfamoyl-benzoic acid 3-(3-methoxybenzylamino)-4-(2-thienyl)-5-sulfamoyl-benzoic acid 3-(4-methoxybenzylamino)-4-(2-thienyl)-5-sulfamoyl-benzoic acid 3-(2-furylmethylamino)-4-(2-thienyl)-5-sulfamoylbenzoic acid 3-(2-furylmethylamino)-4-(3-thienyl)-5-sulfamoylbenzoic acid The following Examples illustrate the invention.

EXAMPLE 1

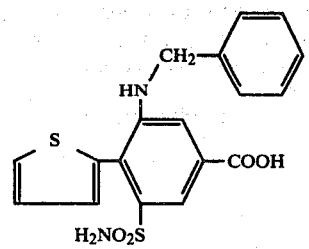

3-Benzylamino-4-(2-thienyl)-5-sulfamoyl-benzoic acid (a) 3-Benzylamino-4-(2-thienyl)-5-N,N-dimethylamino-methyleneaminosulfonyl-benzoic acid methyl ester 11 g 3-Amino-4-(2-thienyl)-5-N,N-dimethylamino-methylene-aminosulfonyl-benzoic acid methyl ester are dissolved in 100 ml dimethyl formamide, and 5 g benzyl bromide are added. The batch is refluxed, and 2 ml triethylamine are added dropwise. After 4 to 5 hours, the reaction mixture is allowed to cool, and subsequently as it is stirred into 500 ml icewater. The precipitated product is crystallized from CH$_3$OH or ethanol. Melting point (m.P.): 163°–165° C.

(b) 9.4 g of the ester obtained according to 1 (a) are suspended in 2 N NaOH and refluxed until a clear solution is obtained. Subsequently, the free acid is precipitated with 2 N HCl in cold state, and the product is recrystallized from glacial acetic acid or CH$_3$OH/H$_2$O. Light yellow needles, m.p. 243°–246° C.

NMR data: (D$_6$-DMSO, 60 MHz, TMS) in ppm: δ=4.4 (d,2H), δ=5.25 (t,1H), δ=6.8–7.5 (m, 10H), δ=7.66–8.0 (m2H).

EXAMPLE 2

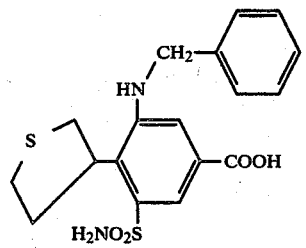

3-Benzylamino-4-(3-thienyl)-5-sulfamoyl-benzoic acid (a) 3-Benzlyamino-4-(3-thienyl)-5-N,N-dimethylaminomethylene-aminosulfonyl-benzoic acid methyl ester 5.5 g 3-Amino-4-(3-thienyl)-5-N,N-dimethylaminomethylene-aminosulfonyl-benzoic acid methyl ester are dissolved in 50 ml dimethyl formamide, 3.5 ml benzyl bromide and 1.5 ml triethylamine are added, and the batch is refluxed for 1.5 hours. Subsequently, the solution is introduced dropwise into icewater, the product is isolated and recrystallized from CH$_3$OH/H$_2$O or CH$_3$OH.

M.p.: 139°–140° C.

(b) 4.9 g of the ester obtained according to 2 (a) are suspended in 2 N NaOH and refluxed until a clear solution is obtained. Subsequently, the product is precipitated in cold state with 2 N HCl and recrystallized from CH$_3$OH/H$_2$O or glacial acetic acid.

Light yellow needles, m.p. 245°–247° C.

NMR data: (D$_6$-DMSO, 60 MHz, TMS) in ppm: δ=4.3 (d,2H), δ=4.9 (t,1H), δ=6.5–7.8 (m,12H)

EXAMPLE 3

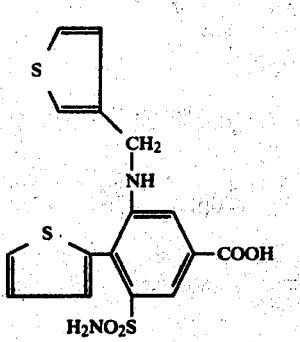

3-(3'-Thenylamino)-4-(2-thienyl)-5-sulfamoyl-benzoic acid 18.4 g 3-Amino-4-(2-thienyl)-5-N,N-dimethylaminomethylene-aminosulfonyl-benzoic acid methyl ester are dissolved in 100 ml absolute dimethyl formamide and refluxed. Subsequently, 35 g 3-thenyl-bromide and 15 g triethylamine are added dropwise with vigorous agitation, simultaneously but separately. After 2 hours, the mixture is concentrated and remaining oil is digested several times with petroleum ether and subsequently with water.

The solid mass remaining is heated on a steam bath with 2 N NaOh until a clear solution is obtained. Subsequently, it is filtered and the pH is adjusted to 3–4 by means of 2 N HCl. The precipitated product can be recrystallized from CH$_3$OH, glacial acetic acid or acetonitrile. Light yellow crystals, m.p. 206°–207° C. NMR-data: (D$_6$-DMSO, 60 MHz, TMS) in ppm: δ=4.31 (d,2H), δ=5.06 (t,1H), δ=6.7–8.0 (m, 10H)

EXAMPLE 4

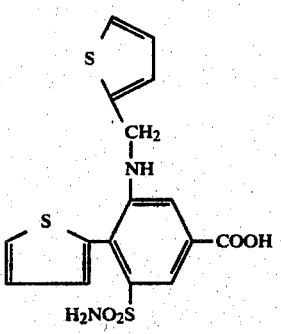

3-(2'-Thenylamino)-4-(2-thienyl)-5-sulfamoyl-benzoic acid (a)
3-(2'-Thenoylamino)-4-(2-thienyl)-5-N,N-dimethylaminomethylene-aminosulfonyl-benzoic acid methyl ester A solution of 0.074 mol (7.9 ml) 2-thenoyl chloride in acetone is added dropwise, slowly and with agitation, to a boiling solution of 0.037 mol (about 13.5 g) 3-amino-4-(2-thienyl)-5-N,N-dimethylaminomethylene-aminosulfonylbenzoic acid methyl ester and 0.045 mol (about 3.6 ml) pyridine in 100 ml absolute dioxan. Part of the product crystallizes already during the reaction. After 2 hours, the batch is filtered and the product is washed well with ether. M.p. 233°–234° C.

(b) 15.9 g (0.033 mol) amide of Example 4(a) are suspended in 450 ml absolute diglyme, and 9.5 ml boron trifluoride etherate are added. Subsequently, a solution of 1.8 g sodium borohydride in 150 ml absolute diglyme is added dropwise at 50° C. and with thorough agitation, and agitation is continued at 50°–70° C. for 2 hours. The product is then precipitated with icewater, isolated and saponified with 2 N NaOH on a steam bath until a clear solution is obtained. On addition of 2 N HCl until a pH of 3–4 is adjusted the 3-(2'-thenylamino)-4-(2-thienyl)-5-sulfamoylbenzoic acid precipitates. Recrystallization from CH$_3$OH or CH$_3$OH/H$_2$O. M.p. 115°–117° C. (highly viscous melt).

NMR data: (D$_6$-DMSO, 60 MHz, TMS) in ppm: δ=4.5 (d, 2H), δ=(t, 1H), δ=6.7–7.5 (m, 8H), δ=7.5–8 (m, 2H)

EXAMPLE 5

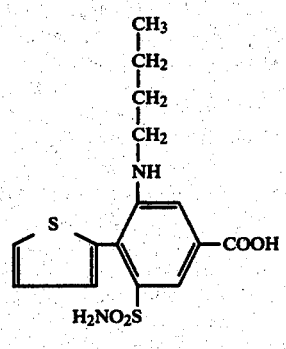

4-(2-Thienyl)-3-N-butylamino-5-sulfamoyl-benzoic acid (a)
3-Butyrylamino-4-(2-thienyl)-5-N,N-dimethylaminomethylene-aminosulfonyl-benzoic acid methyl ester 11.2 g (0.03 mol) 3-Amino-4-(2-thienyl)-5-N,N-dimethylaminomethylene-aminosulfonyl-benzoic acid methyl ester are refluxed in 100 ml absolute dioxan and 3 ml pyridine. Subsequently, 6.4 g butyric acid chloride dissolved in 50 ml acetone are added dropwise. After ½ hour the amide is precipitated with icewater and recrystallized from CH$_3$OH. M.p. 202°–203° C.

(b) 8.1 amide are dissolved in 150 ml absolute diglyme, 4.7 ml BF$_3$ etherate are added, and the batch is warmed to 50° C. A solution of 1.4 g NaBH$_4$ in 100 ml diglyme is added dropwise. After 1 hour, the batch is decomposed with a small amount of water, and subsequently precipitated with icewater. The precipitated crude product is saponified with 2 N NaOH on a steam bath until a clear solution is obtained, and the free acid is then precipitated with HCl at a pH of 3–4. Recrystallization from CH₃OH/H₂O. M.p. 157°–158° C.

NMR data: (D₆-DMSO, 60 MHz, TMS) in ppm: δ=0.5–1.67 (m, 7H), δ=3.06 (m, 2H), δ=4.25 (t, 1H), δ=6.7–7.4 (m, 5H), δ=7.6–7.9 (m, 2H)

EXAMPLE 6

Furfurylamino-4-(2-thienyl)-5-sulfamoylbenzoic acid (a) A solution of 2.86 g furane-2-carboxylic acid chloride in 10 ml acetone is added at room temperature to a mixture of 7.34 g (0.02 mol) 3-amino-4-(2-thienyl)-5-N,N-dimethylaminomethylene-aminosulfonyl-benzoic acid methyl ester and 1.5 g K₂CO₃ in 75 ml acetone, and the reaction mixture is heated to boiling temperature for 90 minutes. After cooling, 50 ml water are added, agitation is continued for 30 minutes with ice cooling, thus causing the 3-(2-furfuroylamido)-4-(2-thienyl)-5-N,N-dimethylaminomethylene-aminosulfonyl-benzoic acid methyl ester to precipitate in the form of cream-colored crystals having a melting point of 216°–218° C., which, after good drying, is directly used for further reactions without special purification.

(b) 1.6 ml BF₃ etherate are added at room temperature to a mixture of 2 g of the above amido compound in 60 ml diglyme, agitation is continued for 15 minutes, and subsequently, a solution of 500 mg NaBH₄ in 50 ml diglyme is added dropwise to the suspension. After 60 minutes at room temperature, agitation is continued for 60 minutes at 60° C., the reaction mixture is cooled and carefully hydrolyzed with water. After the development of hydrogen has stopped, the reaction mixture is poured into 500 ml of water, the precipitated product is extracted with ethyl acetate, and after drying of the organic phase with MgSO₄ the solvent is removed.

The residue is recrystallized from ethanol. The 3-(2-furfurylamino)-4-(2-thienyl)-5-N,N-dimethylamino-sulfonyl-benzoic acid methyl ester is isolated in the form of cream-colored crystals having a melting point of 190°–192° C.

(c) A mixture of 8 g of the 3-(2-furfurylamino)-4-(2-thienyl)-5-N,N-dimethylaminosulfonyl-benzoic acid methyl ester in 200 ml 1 N NaOH is heated for 60 minutes on a steam bath, thus forming a clear solution. After a further 30 minutes on the steam bath, the batch is filtered, cooled and subsequently acidifed with 2 N HCl. The precipitated solids are isolated and recrystallized from methanol/water 1:1. The 3-(2-furfurylamino)-4-(2-thienyl)-5-sulfamoylbenzoic acid is isolated in the form of cream-colored crystals having a melting point of 97°–103° C.

NMR data: (D₆-DMSO, 60 MHz, TMS) in ppm: δ=4.4 (d, 2H), δ=5.0 (t, 1H), δ=6.13 (m, 1H), δ=6.33 (m, 1H), δ=6.9–8.0 (m, 8H)

What is claimed is:

1. A thienylbenzoic acid compound of the formula

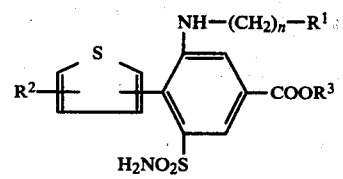

or a pharmaceutically acceptable salt thereof with an acid or base wherein, $R^1$ is phenyl, thienyl, furyl, or is phenyl, thienyl or furyl substituted by halogen, —CF₃, —CH₃, or —OCH₃;

$R^2$ is hydrogen, halogen, or —CH₃;

$R^3$ is hydrogen, alkyl having from 1 to 4 carbon atoms, or benzyl; and n is 1 or 2.

2. A compound as in claim 1 wherein $R^1$ is phenyl, 2-, 3-, or 4-fluorophenyl, 2- or 3-thienyl, or 2- or 3-furyl; $R^2$ is hydrogen; and n is 1.

3. A compound as in claim 1 which is 3-benzylamino-4-(2-thienyl)-5-sulfamoyl benzoic acid.

4. A compound as in claim 1 which is 3-benzylamino-4-(3-thienyl)-5-sulfamoyl-benzoic acid.

5. A compound as in claim 1 which is 3-(3'-thenylamino)-4-(2-thienyl)-5-sulfamoyl-benzoic acid.

6. A compound as in claim 1 which is 3-(2'-thenylamino)-4-(2-thienyl)-5-sulfamoyl-benzoic acid.

7. A diuretic and saluretic pharmaceutical composition comprising a diuretically and saluretically effective amount of a compound or salt as in claim 1 together with a pharmaceutical carrier.

8. A composition as in claim 7 in dosage unit form containing about 0.5 mg to 100 mg. of said compound or salt.

9. The method of treating symptoms arising in a patient from a disturbance of the water and electrolyte balance which method comprises orally or parenterally administering to said patient a diuretically effective amount of a compound or salt as in claim 1.

* * * * *

UNITED STATES PATENT OFFICE
CERTIFICATE OF CORRECTION

Patent No. 4,393,072      Dated July 12, 1983

Inventor(s) Merkel et al.

It is certified that error appears in the above-identified patent and that said Letters Patent are hereby corrected as shown below:

On the cover page, line designated [63] et seq. reading:

"Continuation of Ser. No. is a continuation of Ser. No. 94,059, Nov. 14, 1979, abandoned."

should be changed to read:

--Continuation of Ser. No. 247,401, Mar. 25, 1981, now abandoned, which is a continuation of Ser. No. 94,059, Nov. 14, 1979, abandoned. --

Signed and Sealed this

Twenty-seventh Day of September 1983

[SEAL]

Attest:

GERALD J. MOSSINGHOFF

Attesting Officer     Commissioner of Patents and Trademarks